United States Patent
Nielsen et al.

(10) Patent No.: US 10,379,084 B2
(45) Date of Patent: Aug. 13, 2019

(54) TURBIDITY SENSOR BASED ON ULTRASOUND MEASUREMENTS

(71) Applicant: Kamstrup A/S, Skanderborg (DK)

(72) Inventors: Søren Tønnes Nielsen, Solbjerg (DK); Peter Schmidt Laursen, Skanderborg (DK); Jens Lykke Sørensen, Beder (DK); Sune Hoveroust Dupont, Hasselager (DK)

(73) Assignee: Kamstrup A/S, Skanderborg (DK)

( * ) Notice: Subject to any disclaimer, the term of this patent is extended or adjusted under 35 U.S.C. 154(b) by 0 days.

(21) Appl. No.: 15/741,560

(22) PCT Filed: Jul. 1, 2016

(86) PCT No.: PCT/DK2016/050235
§ 371 (c)(1),
(2) Date: Jan. 3, 2018

(87) PCT Pub. No.: WO2017/005268
PCT Pub. Date: Jan. 12, 2017

(65) Prior Publication Data
US 2018/0188210 A1 Jul. 5, 2018

(30) Foreign Application Priority Data

Jul. 3, 2015 (EP) .................... 15175269
Jul. 3, 2015 (EP) .................... 15175270
Jul. 3, 2015 (EP) .................... 15175271

(51) Int. Cl.
*G01N 29/032* (2006.01)
*G01D 4/00* (2006.01)
(Continued)

(52) U.S. Cl.
CPC .......... *G01N 29/032* (2013.01); *G01D 4/00* (2013.01); *G01D 4/002* (2013.01); *G01D 4/004* (2013.01);
(Continued)

(58) Field of Classification Search
CPC .......... G01N 29/032; G01N 2291/015; G01N 2291/02416; G01N 2291/02408;
(Continued)

(56) References Cited

U.S. PATENT DOCUMENTS 3,849,002 A * 11/1974 Hach .................. G01N 1/28
356/246
4,740,709 A * 4/1988 Leighton ............... G01N 21/05
250/573

(Continued)

FOREIGN PATENT DOCUMENTS

WO 2012129170 A1 9/2012
WO 2013059360 A1 4/2013

OTHER PUBLICATIONS

Anne Rausch et al., Optical measurement of acoustic pressure amplitudes—at the sensitivity limits of Rayleigh scattering, Optics letters, Jul. 1, 2012/vol. 37, No. 13, pp. 2685-2687.*
(Continued)

*Primary Examiner* — Marrit Eyassu
(74) *Attorney, Agent, or Firm* — Renner Otto Boisselle and Sklar LLP

(57) ABSTRACT

A turbidity measurement device for measuring turbidity of a fluid flowing in a flow tube. A first transducer transmits ultrasonic signals through the fluid in the turbidity measurement section so as to provide a first ultrasonic standing wave between the first and second section ends. A receiver transducer receives the ultrasonic scattered response from particles in the fluid flowing through the turbidity measurement
(Continued)

section. A control circuit operates the transducers and generates a signal indicative of the turbidity of the fluid in response to signals received from the receiver transducer. Preferably, the device may comprise a second transducer for generating a second ultrasonic standing wave with the same frequency, and further the two transducers may be used to generate a measure of flow rate by means of known ultrasonic techniques. This flow rate may be used in the calculation of a measure of turbidity. Both turbidity facilities and flow rate facilities may be integrated in a consumption meter, such as a heat meter or a water meter.

19 Claims, 7 Drawing Sheets

(51) Int. Cl.
*G01M 3/24* (2006.01)
*G01F 1/66* (2006.01)
*G01M 3/28* (2006.01)

(52) U.S. Cl.
CPC ............ *G01F 1/666* (2013.01); *G01M 3/243* (2013.01); *G01M 3/2815* (2013.01); *G01N 2291/015* (2013.01); *G01N 2291/02408* (2013.01); *G01N 2291/02416* (2013.01); *G01N 2291/044* (2013.01); *Y02B 90/241* (2013.01); *Y02B 90/242* (2013.01); *Y02B 90/246* (2013.01); *Y04S 20/32* (2013.01); *Y04S 20/322* (2013.01); *Y04S 20/36* (2013.01); *Y04S 20/42* (2013.01)

(58) Field of Classification Search
CPC .......... G01N 2291/044; G01M 3/2815; G01M 3/243; G01D 4/002; G01D 4/004; G01D 4/00; Y02B 90/242; Y02B 90/241; Y02B 90/246; Y04S 20/32; Y04S 20/322; Y04S 20/36; Y04S 20/42; G01F 1/666
USPC ....................................................... 73/61.75
See application file for complete search history.

(56) References Cited

U.S. PATENT DOCUMENTS

| | | | | |
|---|---|---|---|---|
| 5,688,406 | A * | 11/1997 | Dickinson | B01D 21/283 210/170.09 |
| 6,539,812 | B1 * | 4/2003 | Bergamini | G01F 1/662 73/861.29 |
| 7,096,719 | B2 * | 8/2006 | Gysling | G01F 1/667 73/19.03 |
| 2006/0169054 | A1 * | 8/2006 | Keese | G01F 1/58 73/861.12 |
| 2007/0193357 | A1 * | 8/2007 | Daaland | G01B 17/02 73/626 |
| 2014/0238116 | A1 * | 8/2014 | Kwan | G01F 1/667 73/61.79 |
| 2014/0318225 | A1 * | 10/2014 | Kersey | G01N 15/0255 73/61.72 |
| 2016/0335875 | A1 * | 11/2016 | Alcorn | G01F 1/34 |

OTHER PUBLICATIONS

Anne Rausch et al: "Optical measurement of acoustic pressure amplitudes at the sensitivity limits of Rayleigh scattering", Optics Letters, Optical Society of America, US, vol. 37, No. 13, Jul. 1, 2012 (Jul. 1, 2012), pp. 2685-2687, XP001576883, ISSN: 0146-9592, DOI: 10.1364/OL.37.002685.
The International Preliminary Report on Patentability for Corresponding International Application PCT/DK2016/050235 dated May 29, 2017.
The International Search Report and the Written Opinion of the International Searching Authority for Corresponding International Application PCT/DK2016/050235 dated Oct. 25, 2016.
Fischer S.: A new high resolution velocity and acoustic turbidity profiler for open channels, ISUD7 Proceedings (2010), 35-38.

* cited by examiner

TURBIDITY SENSOR BASED ON ULTRASOUND MEASUREMENTS

This application is a national phase of International Application No. PCT/DK2016/050235 filed Jul. 1, 2016 and published in the English language, which is an International Application of and claims benefit of priority to European Patent Application No. 15175269.8, filed on Jul. 3, 2015; 15175270.6, filed on Jul. 3, 2015 and 15175271.4, filed on Jul. 3, 2015. The disclosures of the above-referenced applications are hereby expressly incorporated by reference in their entireties.

FIELD OF THE INVENTION

The present invention relates to the field of turbidity sensors for measurement of turbidity of a fluid. Especially, the invention provides a device capable of measuring turbidity based on ultrasonic measurements. Further, the invention provides an ultrasonic consumption meter, or utility meter, comprising such turbidity sensor.

BACKGROUND OF THE INVENTION

Worldwide the consumption of clean water for drinking is increasing. Drinking water is retrieved from underground wells, but also surface water or even de-salted sea water are used as drinking water. Thus, there is a demand for utility companies to measure cleanness of the water supplied to the utility network.

A complete analysis of cleanness of water involves complicated biochemical analyses, however in some cases a measure of water quality obtained by means of a turbidity measurement can be sufficient, i.e. measurement of the amount of particles in the fluid as a measure of cleanness of the fluid. Such turbidity measurements can be based on optical methods.

Optical turbidity equipment, however, is not well-suited for functioning as a permanently mounted part of a utility network due to the forming of coatings of minerals and/or biofilms on the optical surfaces, which will disturb the turbidity measurements and necessitate frequent maintenance. Furthermore, such optical turbidity measurement equipment is expensive and can thus in practice only be installed at a limited number of positions in a utility network.

SUMMARY OF THE INVENTION

It would be advantageous to provide a simple and low cost turbidity measurement device which is still robust and reliable for measuring turbidity of the fluid in a utility network, hereby allowing utility companies to distribute such devices at several positions in the utility network.

In a first aspect, the invention provides a device arranged to measure turbidity of a fluid flowing in a flow tube, the device comprising:
  a flow tube with a through-going opening for passage of a fluid between an inlet and an outlet and comprising a turbidity measurement section between a first section end and a second section end;
  a first transducer arranged for transmitting ultrasonic signals through the fluid in the turbidity measurement section so as to provide a first ultrasonic wave between the first and second section ends;
  a receiver transducer arranged for receiving ultrasonic signals scattered on particles in the fluid flowing through the turbidity measurement section; and
  a control circuit connected to the first transducer and the receiver transducer, the control circuit being arranged for operating the first transducer and to generate a signal indicative of the turbidity of the fluid in response to signals received from the receiver transducer.

The use of ultrasonic waves for measurement of turbidity provides a reliable and robust way of measuring turbidity without the problems with disturbing coatings which causes problems in optical solutions.

The invention is based on the insight that particles in a fluid will scatter ultrasonic waves in the surrounding fluid.

According to the invention, the ultrasonic wave is generated in a flow tube between two boundaries, e.g. a wave based on applying to the first transducer an ultrasonic pure tone having a frequency $f_0$. A particle moving along with fluid flowing in the flow tube will then pass the acoustic wave, and when passing a zone with high ultrasonic intensity, the particle will scatter ultrasonic waves with the frequency of the wave $f_0$ at a relatively high intensity. Correspondingly, the particle will not scatter any ultrasonic waves when passing a zone with low ultrasonic intensity.

Further according to the invention, after demodulating with frequency $f_0$, the receiver will exhibit a residual oscillation at a frequency, $f_s$, depending on the velocity, v, with which the particles have travelled along the wave. The residual oscillation frequency is given by $f_s=(v/c)f_0$, where c is the phase velocity of the ultrasound in the fluid. By filtering the demodulated signal, allowing only frequencies around $f_s$ to pass, any background contributions from stray reflections etc. can be discriminated, since these, originating from stationary sources, will contribute only to the DC component of the demodulated signal.

Since the scattering probability of typical particles is expected to be small, a high intensity of ultrasound is desired. This can be achieved by employing the flow tube as a resonator to the ultrasound, hence choosing an ultrasound frequency so that the wave after a round trip back and forth in the measurement section will be reflected in-phase with itself. The resulting intensity pattern will be a standing wave, having anti-nodes of high intensity and nodes of low intensity.

With little or no reflections, the standing wave will turn into (a) unidirectional traveling wave(s). Even in this case, however, the device according to the invention will still be able to measure the turbidity since a particle moving with the flow scatters on the traveling wave. The frequency of the scattered ultrasound is downshifted in frequency if the flow and ultrasound propagation is in the same direction and upshifted in frequency if the flow and ultrasound propagation is opposite. This is known as the Doppler shift or Doppler effect. The receiver transducer will detect this frequency-shifted signal. This frequency shift is comparable to the standing wave signal, but will not benefit from the intensity enhancement of the resonator.

Thus it is recognized that even in the absence of a standing wave pattern, the ultrasound scattered by impurities travelling with the fluid and detected at the receiver, will exhibit the frequency $f_s$ after demodulation with the carrier frequency $f_0$. The reason in this case is that the impurities are travelling with velocity v relative to the ultrasonic source and hence experience a Doppler shifted ultrasonic frequency, which is scattered into the receiver.

Back scattering Doppler turbidity sensors are known in the art. These employ only a single transducer acting simultaneously as transmitter and receiver. The demands to such a transducer are quite severe, since the oscillations from signal transmission must have died out at the time the echo reaches the transducer. Hence, the transducer must be efficiently mechanically damped, which in turn limits the coherence of the ultrasonic wave and hence the accuracy of the sensor. Utilizing several transducers as is proposed in the present invention, allows for optimizing these for their respective functions in the sensor and elimination of the above problem. Hence, the transmitter can be designed to oscillate at a high Q-value resonance resulting in high coherence, high intensity and high quality wave propagation pattern, and the dedicated receiver can be designed to have high bandwidth and high sensitivity resulting in high frequency resolution of the scattered ultrasonic waves.

Also in the case of oblique angles between sound and fluid propagation the oscillation frequency is modulated according to $f_s=(v/c)f_0 \cos \varphi$, where $\varphi$ is the angle between sound propagation direction and mean fluid velocity.

Thus it is to be understood that according to the invention the first transducer may be arranged at said first section, creating a travelling wave propagating either parallel, anti-parallel or at an oblique angle different from 90 degrees relative to the mean fluid velocity. The receiving transducer may be arranged perpendicular to the travelling wave propagation direction so that no reflections apart from the desired scattered signal are detected. The electronic signal derived from the receiving transducer is demodulated with the ultrasonic frequency $f_0$ and the resulting signal is spectrally analysed to yield a quantity indicative of the turbidity level as the spectral density in a frequency band around $f_s$.

In an embodiment the first and second transducers are operating in a transient mode, where they emit wavepackets shorter than the length of the measurement section. Hence, the measurement section cannot perform as a resonator but a transient standing wave pattern will still occur in the region of the measurement section, where the wavepackets collide. As a result the demodulated signal from the receiver will still exhibit the frequency $f_s$, but the technical complexity associated with tracking the resonance of the measurement section is reduced. Noise suppression and improvement of signal to noise ratio may be achieved by synchronizing the receiver with the wavepacket generation using standard lock-in techniques.

The ultrasonic transducers may occasionally be operated in a fashion appropriate for a time-of-flight or Doppler flow meter. It is reasonable to assume that the particles move with the same velocity as the fluid, hence the flow measurement readily yields the value of v, using two transducers. Consequently, knowledge of the fluid velocity implies that the expected values of $f_s$ is known, meaning that an adaptive digital filter can be employed to select a band around this frequency thereby rejecting background noise. Such filtering techniques are well known in the art of digital signal processing.

In practice the speed of sound, c, varies appreciably with the temperature of the fluid. The ultrasonic flow meter operation mode of the turbidity sensor may accordingly also be utilised to provide a measurement of the fluid temperature as well. This becomes apparent, since the essence of the time-of-flight flow measurement is the timing of two ultrasonic wave packets travelling between two transducers co- and counter-propagating to the fluid flow respectively. The length of the measurement section divided by the average travelling time of the two wave packets results in the speed of sound in the fluid.

Alternatively, a separate, dedicated temperature sensor may be included in the turbidity sensor in order to determine the temperature dependent value of c by means of a lookup table.

It is to be understood that it is still possible to provide a measure of turbidity without a measure of flow rate of the fluid, however, resulting in reduced reliability. Alternatively, a more complicated signal processing will in such case be necessary in order to provide a reliable measure of turbidity.

Also it should be understood that c is temperature dependent. Although it is still possible to provide a measure of turbidity based on temperature estimates, a more reliable turbidity measurement may be obtained in those cases of in-situ measurements of the fluid temperature, e.g. by means of a temperature sensor integrated with the device.

In the long wavelength regime, the power of ultrasonic waves scattered from a particle is proportional to the $4^{th}$ power of the ultrasonic wave frequency, and proportional to the $2^{nd}$ power of the volume of the particle. For example, this means that the ultrasonic response from particles with a size of 5-10 µm, e.g. larger colloides, grains of sand, particles of clay, organic material etc. can be observed using an ultrasonic standing wave at a frequency $f_0$ being in the MHz range, e.g. 5-10 MHz. Quantifying the amount of such particles provides a measure of turbidity of a fluid, e.g. water in a drinking water utility network, which is a useful measure of general cleanness of the fluid. The technique may even have a sensitivity allowing for the detection of microbes, amoebae and bacteria in sufficiently high concentrations.

Generation and measurements of ultrasonic waves in the MHz frequency range is possible by normal low cost components, and thus similar technology as known in ultrasonic flow meters. Thus, a turbidity measurement device can easily be combined and integrated with existing ultrasonic flow meters, e.g. as known in ultrasonic consumption meters. Hereby, the turbidity measurement facility can be provided by a single component without the need for installing a separate device to monitor turbidity of a fluid in a utility network. Even further, it is advantageous to combine the turbidity device with an ultrasonic flow meter, since hereby the flow rate can be provided for use in the turbidity calculation, as explained above. By integrating the turbidity functionality into a consumption meter, the wireless communication network of such consumption meters can be used for turbidity data as well, thereby allowing collection of turbidity data from the location of a large number of consumers, e.g. for further processing which can help to determine the location of a source of contamination in the piping network.

It is to be understood that the first and the second 'section end' indicate ends of the turbidity measurement section, i.e. ends of the section wherein the ultrasonic wave extends along the fluid direction in the flow tube.

By 'control circuit' is understood the necessary electronic circuits adapted to control the function of the ultrasound transducer(s), i.e. to generate electric signals to drive the first transducer, and to receive electric signals from the receiver transducer.

In the following, preferred features and embodiments will be described.

The first transducer may be arranged at said first section end, and wherein a reflecting element is arranged at the second section end, e.g. to constitute the second section end, for reflecting the ultrasonic signals. Especially, the first transducer may be arranged at a central part of the flow tube cross sectional area and facing an ultrasonic reflecting element also arranged at a central part of the flow tube cross sectional area, e.g. such as at a distance of 5-15 cm from the first transducer, thus allowing the ultrasonic wave become a standing wave between the first transducer and the reflecting element. The first transducer and the reflecting element preferably occupy only a limited fraction of the flow tube cross section area, so as to allow the fluid to flow around these parts without creating any significant disturbance or turbulence in the fluid.

The device may comprise a second transducer arranged at the second section end, so as to provide a second ultrasonic wave between the second and first section ends, and wherein the control circuit is arranged for operating both of the first and second transducers. Preferably, the control circuit is capable of driving the first and second transducers to generate said first and second ultrasonic waves simultaneously. The first and second ultrasonic waves may have similar frequencies, thus the control circuit may be arranged to apply electrical signals, e.g. pure tone signals, with the same frequency e.g. within 1-100 MHz, or more specifically within 2-20 MHz, such as 5-10 MHz. Especially, the same electrical signal may be applied to both of the first and second transducers. Alternatively, the first and second ultrasonic waves may have different frequencies. E.g. a frequency of the first ultrasonic wave may be a rational number p/q times the second frequency of the second wave. This may be advantageous, since in order to provide a high acoustic output, the transducers used may be driven near or at their mechanical resonance frequency, and thus using the same type of transducer for the first and second transducers, driving one transducer at an odd harmonic of its mechanical resonance frequency will still provide a high acoustic output. Further, a frequency of the first ultrasonic wave and a second frequency of the second ultrasonic wave may differ by 0.1% to 10%. The first and second waves are preferably spatially overlapping, e.g. with the first and second transducers arranged at the respective first and second section ends.

In this context, the invention further provides an ultrasonic flow meter comprising first and second ultrasonic transducers arranged to generate respective first and second ultrasonic waves in a flow tube, wherein the a first frequency of the first ultrasonic wave is different from a second frequency of the second ultrasonic wave. The flow meter comprises a control circuit connected to operate the first and second transducers, and being arranged to generate an output indicative of a flow rate of the fluid in the flow tube, preferably in response to sensing an ultrasonic response from scattering on particles of the fluid flowing along the first and second ultrasonic waves. Reference is made to the foregoing paragraph with respect to embodiments of such flow meter with respect to how the frequencies of the first and second ultrasonic waves may be different.

The control circuit may be arranged to generate the signal indicative of the turbidity of the fluid in response to signals received from the receiver transducer and a flow rate of the fluid. Especially, as already mentioned, in case of an ultrasonic wave with frequency $f_0$, the expected signal frequency $f_0 \pm f_s$ of ultrasonic waves received by the receiver transducer is: $f_s = (v/c)f_0 \cos \varphi$. Here $\varphi$ is the angle between sound propagation direction and mean fluid velocity direction, v is the velocity of the particles responsible for the turbidity and c is the speed of the ultrasonic wave in the fluid. This is preferably utilized in the processing in the control circuit, e.g. to demodulate the received signal from the receiver transducer, and to subsequently filter the resulting signal, so as to observe the expected frequency $f_s$ in order to suppress background noise, and thus provide a more reliable measure of turbidity. Especially, the control circuit may be arranged to generate the signal indicative of the turbidity of the fluid in response to an output from a predetermined algorithm in response to both of: a measured flow rate of the fluid in the flow tube, and a frequency of the ultrasonic standing wave. E.g. said predetermined algorithm may involve calculating a level of the ultrasonic signals received by the receiver transducer at one or more frequency components selected in response to both of: the measured flow rate of the fluid in the flow tube, and the frequency of the ultrasonic standing wave.

In an embodiment of the invention the first ultrasonic wave is a standing wave.

In an alternative embodiment of the invention the first ultrasonic wave is a travelling wave.

In an embodiment of the invention the first and the second ultrasonic waves are standing waves.

In an alternative embodiment of the invention the first and the second ultrasonic waves are travelling waves.

The application of standing waves provides areas of high acoustic intensity at the antinodes of the wave, and thus high scattering intensity.

Compared to the application of travelling waves, the application of travelling waves, i.e. non-standing waves, provides higher freedom-of-design of the device.

With an embodiment of the invention the first and second ultrasonic waves are transient waves of similar frequency in the form of wave packets, which are shorter than the distance between the first section end and the second section end, so as to form a transient standing wave in at least part of the turbidity measurement section.

The device may comprise flow measurement means so as to provide a flow rate to be used by the control circuit to calculate a more reliable measure of turbidity, as explained above. The flow rate may be provided by an external device, or it may be measured by an integral flow meter of the device itself. Especially, the flow measurement means may comprise the first transducer, and preferably also a second transducer, and a control circuit operating the first and second transducers according to a time-of-flight or Doppler principle. Hereby, a combined flow meter and turbidity meter can be provided utilizing the same ultrasound transducer and control circuit. Especially, the control circuit may be arranged to operate the first transducer in a first and a second operation time intervals, wherein the first and second operation time intervals are not overlapping, wherein the control circuit is arranged to operate the first transducer for measuring the turbidity of the fluid flowing in the flow tube during the first operation time interval, and wherein the control circuit is arranged to operate the first transducer for measuring the flow rate of the fluid flowing in the flow tube during the second operation time interval. This allows reliable flow rate and turbidity measurements without interference between the ultrasonic signals involved in the two types of measurements, even though the same transducer, or the same set of transducers, are involved in both types of measurements.

The control circuit may be arranged to operate the first transducer at a first frequency for measuring the turbidity, and being arranged to operate the first transducer at a second frequency for measuring the flow rate, such as the first frequency being higher than the second frequency, such as the first frequency being the odd harmonic, like the third harmonic of the first frequency. This frequency difference allows flow rate to be measured at a reasonably low frequency, while turbidity measurements can be provided at a higher frequency to increase sensitivity to detect small particles in the fluid. Especially, the first frequency may be above 1 MHz, such as above 10 MHz, and wherein the second frequency is below 5 MHz, such as below 2 MHz.

The control circuit may be arranged to calculate a level of ultrasonic signals received by the receiver transducer, and to generate the signal indicative of the turbidity of the fluid accordingly, without any knowledge about fluid flow rate in the flow tube. For some applications, the turbidity precision that can be obtained in this way may be sufficient, however a more complicated data processing may be required compared to methods utilizing fluid rate—either provided from an external device, or by the integration of the turbidity device with a flow meter, as already described.

The control circuit may be arranged to generate the signal indicative of the turbidity of the fluid in response to an average of measured values over a period of time, hereby allowing only a limited amount of measured turbidity values to be communicated.

The device may comprise temperature measurement means arranged to measure a temperature of the fluid. Especially, said temperature measurement means may comprise the first transducer, and preferably also a second transducer. Thus, in some embodiments, the first transducers may be used for turbidity measurements, flow rate measurements, as well as temperature measurements.

The device may comprise a first ultrasonic reflector arranged to guide ultrasonic signals from the first transducer in a direction opposite the flow direction in the turbidity measurement section. In embodiments comprising a second transducer, a second ultrasonic reflector may be arranged to guide ultrasonic signals from the second transducer in a direction of the fluid flowing. Especially, such first and 10 second ultrasonic reflectors may constitute the first and second end sections between which the ultrasonic wave extends. Such reflectors allow the first (and possibly second) transducer(s) to be arranged away from a central part of the fluid flow, e.g. with the(se) transducer(s) to be positioned at or near the wall of the flow tube.

Also according to the invention the receiver may have a receiving surface which is parallel to a direction of the first ultrasonic wave.

The device may comprise an acoustic lens or an aperture arranged in relation to the receiver transducer, so as to limit area volume of the turbidity measurement section from which ultrasonic signals can reach the receiver transducer and so discriminate against unwanted background from stray scattering of ultrasound.

The receiver transducer may be arranged in an opening in a wall of the flow tube, such as the receiver transducer being arranged with its receiver surface retracted behind a surface covering said opening. Thus, the receiver transducer may be retracted in a well, thus serving to reduce unwanted ultrasonic reflections from the flow tube in reaching the receiver transducer, thereby increasing the turbidity measurement precision. The receiver transducer is preferably arranged between the first and second section ends, e.g. centrally between said section ends, such as with its receiver surface forming a plane containing the flow direction of the fluid flowing in the turbidity measurement section.

Such arrangements of the receiver transducer allow for efficient reception of scattered signal at high signal-to-noise ratio.

The receiver transducer may comprise a plurality of separate transducers arranged at respective positions along the turbidity measurement section. Such array of separate receiver transducers spatially distributed along the ultrasonic standing wave may provide an improved response signal for further processing compared to a single received transducer.

The first transducer may comprise a piezoelectric transducer. Especially, the piezoelectric transducer may exhibit a mechanical resonance frequency coinciding with a frequency of a drive signal applied to the piezoelectric transducer by the control circuit. This allows the transducer to provide a high acoustic output, and thus provide an ultrasonic standing wave with a high intensity, thereby allowing scattered signals from particles in the fluid to allow a robust turbidity measurement. Especially, the control circuit may be arranged to operate the first transducer at said mechanical resonance frequency for measurement of flow rate, and wherein the control circuit is arranged to operate the first transducer at a higher frequency for measurement of turbidity, and wherein said higher frequency is selected to coincide with an odd harmonic of said mechanical resonance frequency. Hereby, the same transducer can be used to provide a high acoustic output at the two different frequencies for turbidity and flow measurements, respectively.

The first transducer may be arranged in a central part of a cross section of the flow tube, and e.g. constitute the first section end.

The receiver transducer may comprise a piezoelectric transducer.

The device may comprise a liner formed by a material comprising a polymer for covering at least part of a surface of a measurement tube in the turbidity measurement section.

In some embodiments, the device may be integrated or combined with an ultrasonic flow meter which may be or may be part of a charging consumption meter or utility meter, e.g. a water meter for cold and/or hot water, a heat meter, a cooling meter, or a gas meter, where the consumption meter is arranged for measuring consumption data of a supplied utility used as a basis for billing. The consumption meter may be used in connection with district heating, district cooling and/or distributed water supply. The consumption meter may be a legal meter, i.e. a meter which is subdued to regulatory demands. Such regulatory demands may be demands to the precision of the measurements.

Advantageously, the flow meter can be used as a water meter, thus allowing measurement of the amount of particles (i.e. turbidity) in the supplied water.

Especially, in case the device comprises an ultrasonic flow rate capability, the control circuit preferably comprises a measurement circuit to allow measurement of fluid flow according to known principles of ultrasonic transit time. Especially, the measurement circuit may be arranged on one single printed circuit board (PCB) capable of generating as output a pulse train indicative of the measured fluid flow rate. One single processor may be used to handle measurement of both flow rate and turbidity, however separate processors may as well be provided for calculation of flow rate and turbidity.

The device may comprise a communication module connected to the control circuit and arranged for communicating the signal indicative of the turbidity of the fluid, e.g. turbidity data may be communicated as a wireless radio frequency signal.

A specific embodiment of the first aspect provides a device, wherein the first transducer is arranged at the first section end, and wherein a second transducer is arranged at the second section end, so as to provide a second ultrasonic standing wave between the second and first boundaries, and wherein the control circuit is arranged for operating both of the first and the second transducers, wherein the control circuit is arranged to generate the signal indicative of the turbidity of the fluid in response to signals received from the receiver transducer and a flow rate of the fluid, further comprising flow measurement means arranged to measure the flow rate of the fluid flowing in the flow tube, wherein said flow measurement means comprises the first and second transducers, wherein the control circuit is arranged to operate the first and second transducer in a first and second operation time intervals, wherein the first and second operation time intervals are non-overlapping, wherein the control circuit operates the first and second transducers for measuring the turbidity of the fluid flowing in the flow tube during the first operation time interval, and wherein the control circuit operates the first and second transducers for measuring the flow rate of the fluid flowing in the flow tube during the second operation time interval.

Such device is advantageous, since it can use a set of ultrasonic transducers known from existing ultrasonic flow meters, e.g. ultrasonic consumption meters, thus with limited modifications it is possible to provide a device capable of providing a measure of turbidity of the fluid. Especially, it may be considered to be advantageous to use a higher ultrasonic frequency, e.g. higher than 5 MHz, e.g. 10 MHz, for the turbidity measurement, while a lower ultrasonic frequency can be used, e.g. 1-2 MHz for the flow measurements. The device may further comprise a wireless communication module arranged to transmit both of: data indicative of the measured turbidity, and data indicative of the measured flow rate and/or a consumed amount, so as to allow remote reading of turbidity over the same communication channel used for remote reading of utility data.

In the second aspect, the invention provides an ultrasonic consumption meter comprising a device according to the first aspect, such as the ultrasonic consumption meter being a water meter, a gas meter, a heat meter, or a cooling meter.

In a third aspect the invention provides a system for monitoring turbidity of fluid in a utility network, the system comprising a plurality of devices or ultrasonic consumption meters according to the first or second aspects, wherein each of the plurality of devices are arranged to transmit signals indicative of the turbidity of the fluid, and a communication system arranged to mediate said signals indicative of the turbidity of the fluid from the plurality of devices or ultrasonic consumption meters. Optionally, the system may comprise a processor system arranged to analyze said signals indicative of the turbidity of the fluid.

In a fourth aspect, the invention provides a method of measuring turbidity of a fluid flowing in a turbidity measurement section of a flow tube, the method comprising:

transmitting ultrasonic signals from a first transducer to generate an ultrasound wave between a first section end and a second section end, receiving, by means of a receiver transducer, ultrasonic signals scattered on particles in the fluid, and generating a signal indicative of the turbidity of the fluid in response to signals received from the receiver transducer.

The same advantages mentioned for the first aspect apply as well for the second, third, and fourth aspects. In general, the various aspects of the invention may be combined and coupled in any way possible within the scope of the invention.

These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
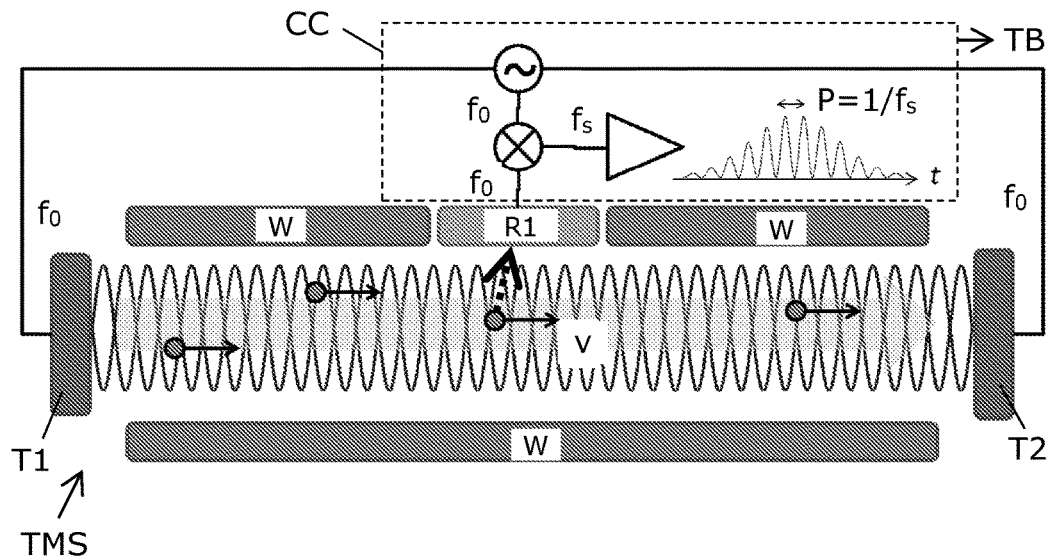
FIG. 1 illustrates a sketch of an embodiment with two transducers generating an ultrasonic standing wave between them, and the receiver transducer arranged at the wall of the flow tube.

FIG. 1 illustrates a sketch of a turbidity measurement device embodiment with a flow tube with walls W, where two transducers T1, T2 are arranged in the flow tube and serve as end sections for the turbidity measurement section TMS between which two ultrasonic standing waves are generated. The dark circles indicate particles flowing along the fluid in the flow tube with flow rate v. A receiver transducer R1 is arranged at the wall W of the flow tube at a central position between the two transducers T1, T2. For one particle an ultrasonic response to the ultrasonic standing wave is indicated with a dashed arrow towards the receiver transducer R1 which then captures the ultrasonic response from the particle. With an ultrasonic standing wave with frequency $f_0$, the expected frequency $f_s$ of high intensity scattering of a particle in a fluid with flow rate v is: $f_s=(v/c)f_0$, where c is the speed of the ultrasonic wave in the fluid. Thus, a high intensity response from particle scattering of the ultrasonic standing wave can then be expected with a period time of $P=1/f_s$ at the receiver transducer, as indicated in the response versus time t to the upper right corner of FIG. 1.

A control circuit CC comprises an electric generator that applies electric drive signals to the transducers T1, T2 at the single frequency $f_0$, receives the response from the receiver transducer R1 and generates in response a signal indicative of turbidity TB. As indicated, the signal from the generator may be applied to a multiplier together with the response from the receiver transducer R1, thus demodulating the received signal. Further, the control circuit CC preferably applies a filtering, e.g. involving Fast Fourier Transform finite impulse response or infinite impulse response digital filters, so as to explore the actual high intensity response from particles at the expected periodicity P. The resulting signal can then be quantified so as to provide a measure of particle density in the fluid, i.e. a measure of turbidity.

It is to be understood that the same two transducers T1, T2 can be used as well for ultrasonic flow rate measurement, such as known in the art, and thus preferably the flow rate v can be measured with the device as well, thus delivering the flow rate v to the control circuit, thereby allowing the above described calculation of $f_s$.

Not shown, the receiver transducer R1 may be retracted from the flow tube wall W, so as to receive only ultrasonic response from a limited portion of the flow tube, rather than all response including reflections.

Figure 2:
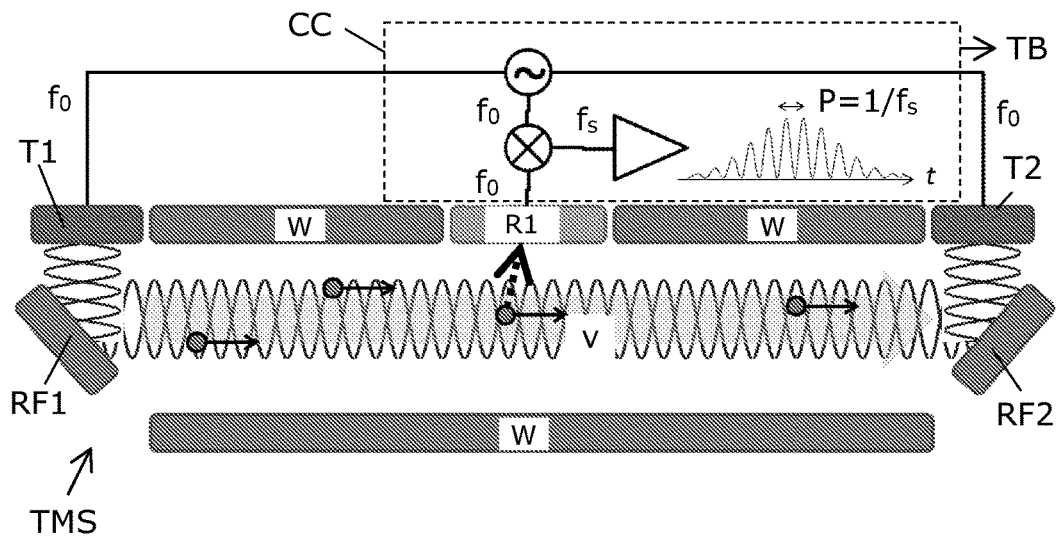
FIG. 2 illustrates a sketch of an embodiment similar to that of FIG. 1 but with reflectors serving to direct ultrasonic waves from the two transducers.

FIG. 2 shows an embodiment similar to FIG. 1 except for the position of the two transducers T1, T1, since here section ends of the turbidity measurement section TMS are constituted by respective ultrasonic reflectors RF1, RF2, e.g. polymeric, composite, or metallic reflectors. Thus, the transducers T1, T2 are positioned out of the fluid flow, along the wall W of the flow tube, and their ultrasound signals are then directed in the flow direction, such that the ultrasonic standing waves between the reflectors is along the flow direction.

Figure 3:
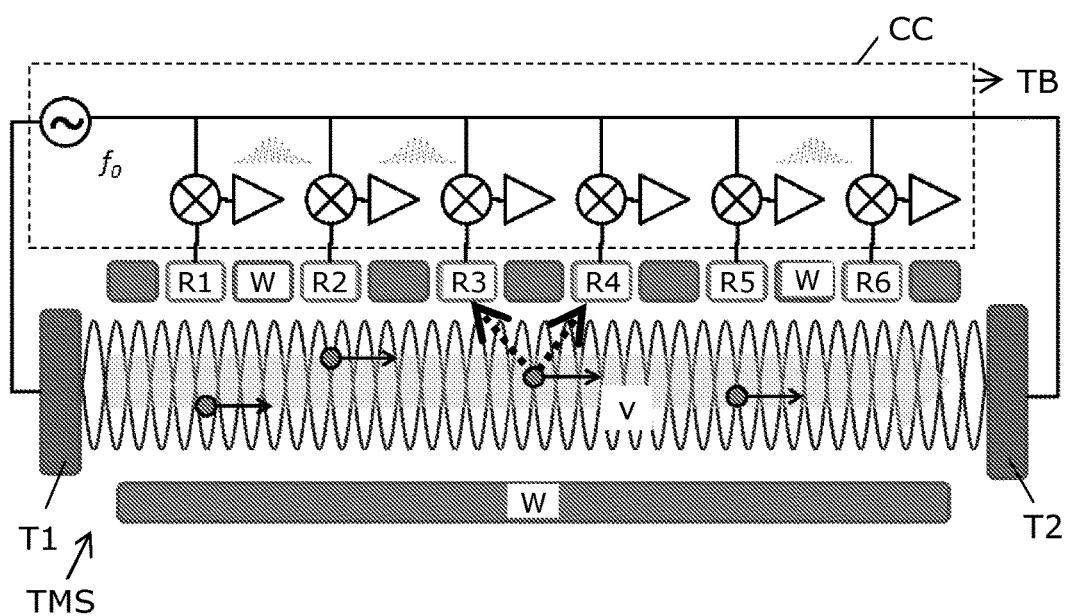
FIG. 3 illustrates an embodiment similar to FIG. 1 but with a plurality of receiver transducers distributed along the flow tube.

FIG. 3 shows an embodiment similar to FIG. 1 except for the use of 6 separate receiver transducers R1-R6 arranged along the flow tube wall. The responses from these receiver transducers R1-R6 are then combined in the processing of the control circuit to result in one single measure of turbidity TB.

Figure 4:
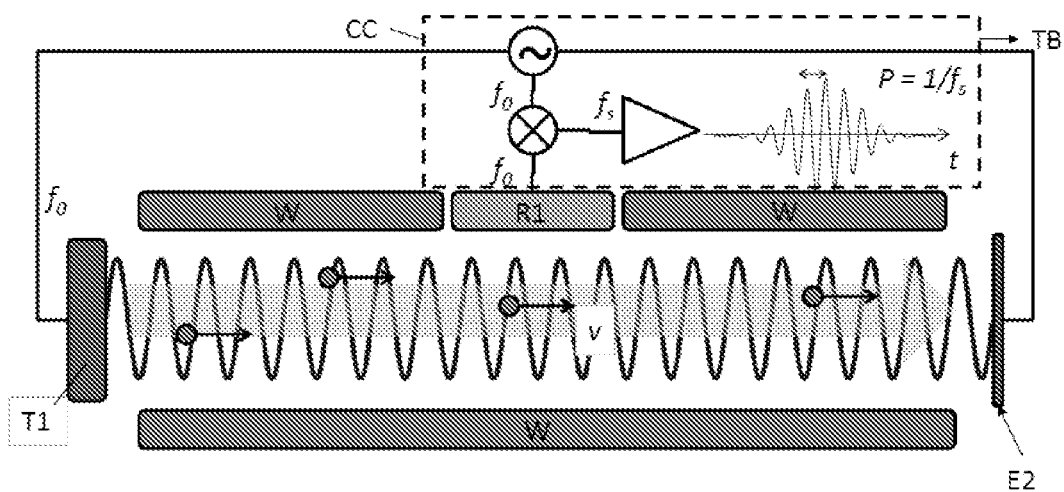
FIG. 4 illustrates a sketch of an embodiment with one transducer generating an ultrasonic travelling wave, and the receiver transducer arranged at the wall of the flow tube.

FIG. 4 illustrates an alternative embodiment of the invention. Compared to the embodiment of the invention of FIG. 1, this embodiment comprises only one transducer T1, and the ultrasonic wave is a travelling wave, i.e. a non-standing wave, as it is only scarcely reflected at the section end E2, or not at all.

The intensity response from particle scattering will not be enhanced by the cavity build up enhancement factor, but it will still exist owing to the Doppler effect. The expected frequency remains $f_s$, as described above.

Figure 5:
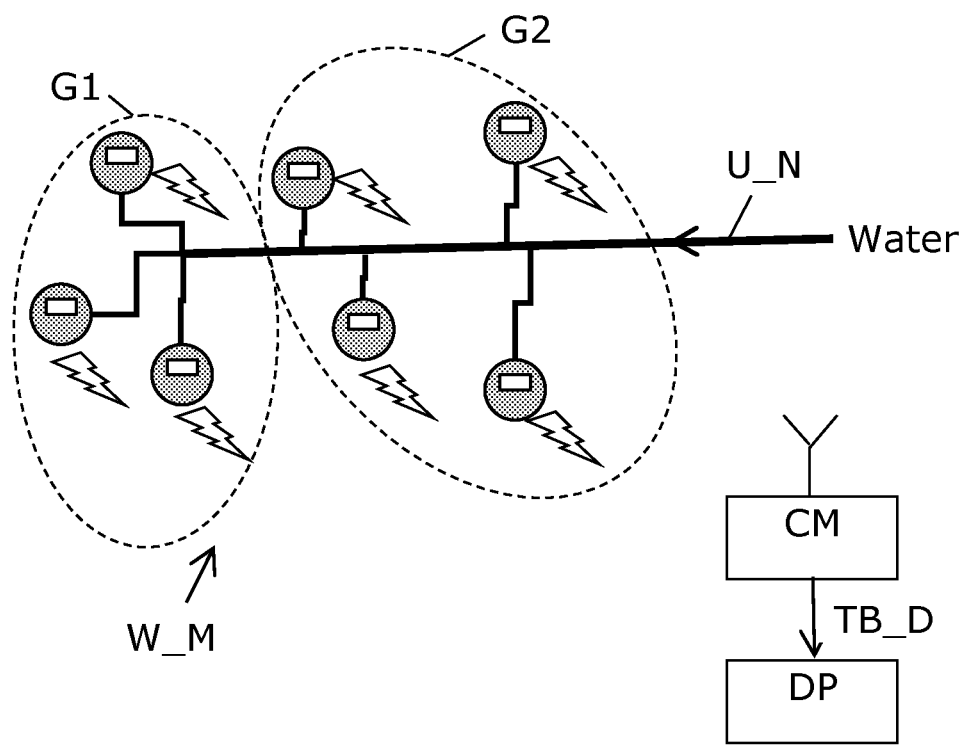
FIG. 5 illustrates a system embodiment with a plurality of water meters with turbidity measurement facilities connected to a utility net and communicating turbidity data to a central facility for processing.

FIG. 5 shows a system embodiment. Two groups G1, G2 of water meters W_M are connected to measure consumed water at respective consumers on a water utility network U_N. The water meters W_M are arranged to measure turbidity according to the present invention, preferably using one or two ultrasonic transducers which are also involved in flow rate measurement for generating a measure of consumed water. Consumed water data and turbidity data are transmitted wirelessly by the water meters W_M to a central communication module which extracts the turbidity data TB_D which are then applied to a data processing DP for further analysis. E.g. in case turbidity is generally higher in group G1 than group G2, it may be used as an indicator that a leak in the piping system between the positions of the two groups G1, G2 of water meters W_M allows soil or other contamination in the water utility network U_N, and thus helps in finding such broken pipe. Otherwise, the turbidity data TB_D may be used to generally monitor water quality delivered to the consumers.

Figure 6:
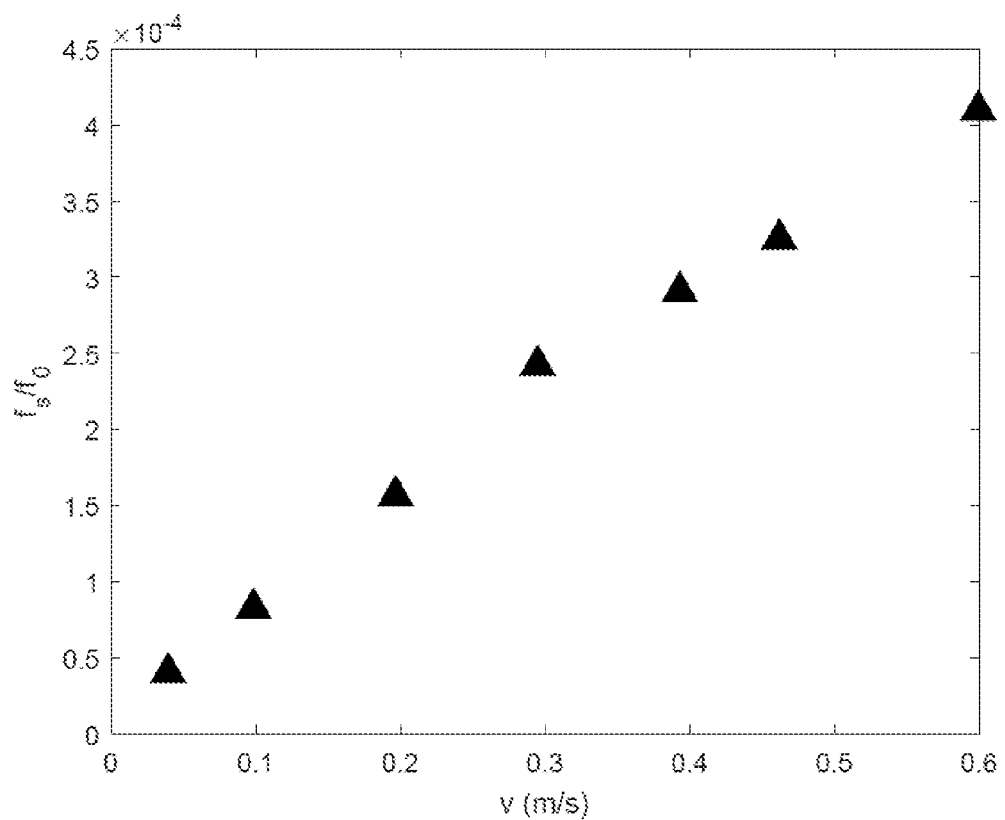
FIG. 6 shows the variation of the residual frequency $f_s$ with the flow velocity v.

FIG. 6 shows the variation of the residual frequency $f_s$ with the flow velocity v.

A device according to the invention as sketched with FIG. 1 was connected to a flow system having a constant turbidity. The transducer was driven with a constant frequency in the range 5-15 MHz and an external time-of-flight flow meter was measuring the flow rate. The signal from a receiver transducer, placed in the turbidity measurement section, was collected and its frequency shift $f_s$ analyzed. The flow velocity based on flow measurement is shown on the x-axis. The y-axis represent the frequency shift where the carrier frequency has been used as units. As can be seen from the figure, the frequency shift varies linearly with flow velocity according to the principle of the residual oscillation frequency of the invention.

Figure 7:
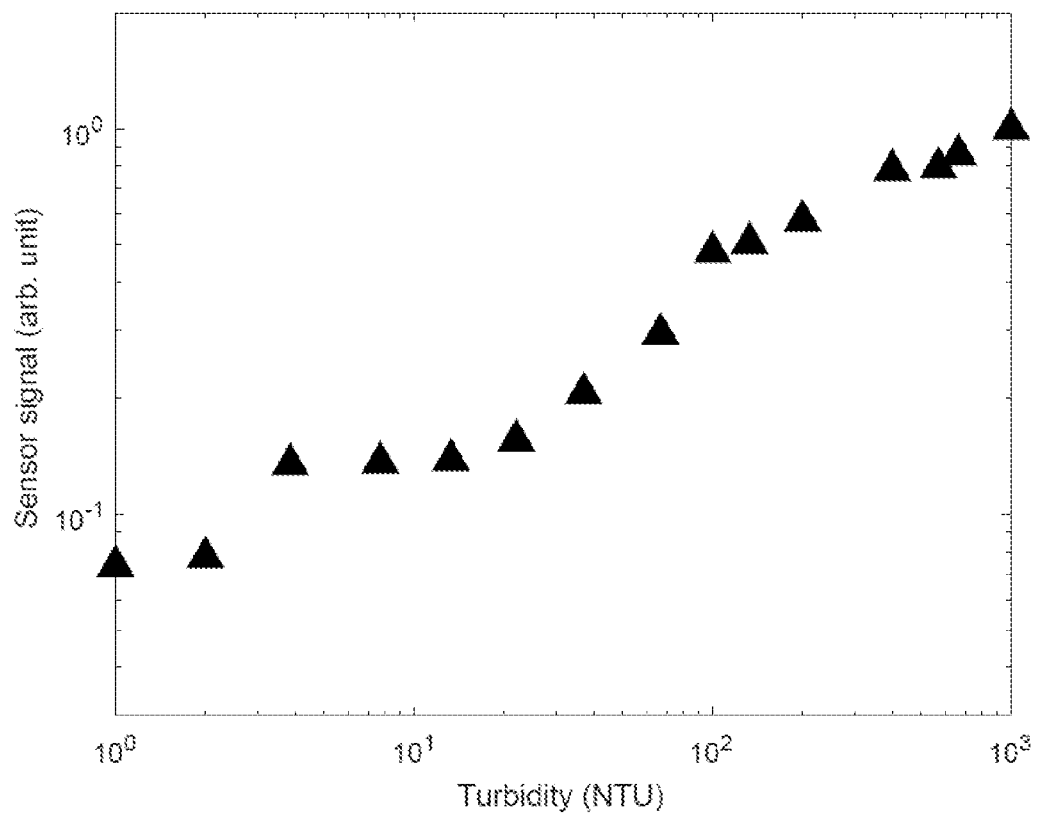
FIG. 7 shows the variation of the intensity of the frequency shifted signal vs. the turbidity level.

FIG. 7 shows the variation of the intensity of the frequency shifted signal vs. the turbidity level.

The setup described in FIG. 6 was employed with a constant flow velocity, i.e. the frequency shift is constant. A series of measurement with varying turbidity (based on a 4000 NTU polystyrene standard) of the fluid flow was conducted. The intensity of the frequency shifted signal is analyzed and plotted as a function of the turbidity. A clear monotonic correspondence is seen between the turbidity and receiver response, even over the broad operational range of the sensor.

Figure 8:
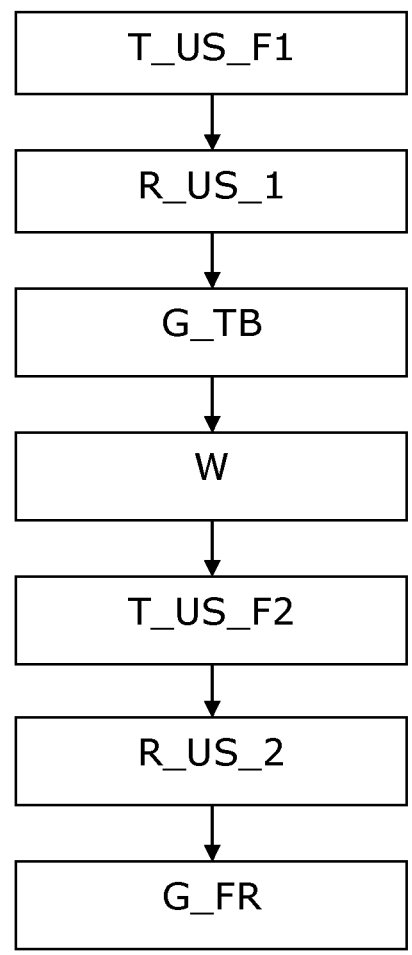
FIG. 8 illustrates steps of a method embodiment.

FIG. 8 shows steps of a method embodiment for measurement of turbidity of a fluid flowing in a flow tube. First, an ultrasound signal is transmitted T_US_F1 at a first frequency from a first transducer trough the fluid, to generate a first ultrasonic standing wave in the flow tube. A response is received R_US_1 by means of a receiver transducer capturing ultrasonic signals scattered on particles in the fluid, and generating G_TB a signal indicative of the turbidity of the fluid in response to signals received from the receiver transducer. Further, another ultrasonic signal is transmitted T_US_F2 from the transducer at a second frequency which is lower than the first frequency. A response thereto is received R_US_2 at a second transducer, and in response a signal indicative of flow rate of fluid flowing in the flow tube is generated G_FR accordingly. Preferably, this flow rate is used in the generation of the signal indicative of the turbidity.

To sum up, the invention provides a turbidity measurement device for measuring turbidity of a fluid flowing in a flow tube. A first transducer transmits ultrasonic signals through the fluid in the turbidity measurement section so as to provide a first ultrasonic wave between the first and second section ends. A receiver transducer receives the ultrasonic scattered response from particles in the fluid flowing through the turbidity measurement section. A control circuit operates the transducers and generates a signal indicative of the turbidity of the fluid in response to signals received from the receiver transducer. Preferably, the device may comprise a second transducer for generating a second ultrasonic wave with the same frequency, and further the two transducer may be used to generate a measure of flow rate by means of known ultrasonic techniques. This flow rate may be used in the calculation of a measure of turbidity. Both turbidity facilities and flow rate facilities may be integrated in a consumption meter, such as a heat meter or a water meter.

Although the present invention has been described in connection with the specified embodiments, it should not be construed as being in any way limited to the presented examples. The invention can be implemented by any suitable means; and the scope of the present invention is to be interpreted in the light of the accompanying claim set. Any reference signs in the claims should not be construed as limiting the scope

The invention claimed is:

1. A device arranged to measure turbidity of a fluid flowing in a flow tube, the device comprising:
   a flow tube having a through-going opening for passage of a fluid between an inlet and an outlet and a turbidity measurement section between a first section end and a second section end,
   a first transducer arranged to transmit ultrasonic signals through the fluid in the turbidity measurement section so as to provide a first ultrasonic wave between the first and second section ends, flow measurement means, wherein said flow measurement means comprises the first transducer;
a receiver transducer arranged for receiving ultrasonic signals scattered on particles in the fluid flowing through the turbidity measurement section, wherein the receiver transducer has a receiving surface which is parallel to a propagation direction of the first ultrasonic wave, and
a control circuit connected to the first transducer and the receiver transducer, the control circuit being arranged to operate the first transducer and to generate a signal indicative of the turbidity of the fluid in response to signals received from the receiver transducer, wherein:
the control circuit is arranged to operate the first transducer at a first frequency for measuring the turbidity, and is further arranged to operate the first transducer at a second frequency for measuring flow rate;
the first frequency is higher than the second frequency; and
the first frequency is an odd harmonic of the second frequency.

2. The device according to claim 1, wherein the first transducer is arranged at said first section end, and wherein a reflecting element is arranged at the second section end for reflecting the ultrasonic signals.

3. The device according to claim 1, wherein a second transducer is arranged at the second section end, so as to provide a second ultrasonic wave between the second and first section ends, and wherein the control circuit is arranged to operate the first transducer and the second transducer.

4. The device according to claim 3, wherein the first and second ultrasonic waves have similar frequencies.

5. The device according to claim 3, wherein a frequency of the first ultrasonic wave is a rational number p/q times a frequency of the second wave, or wherein a frequency of the first ultrasonic wave and a frequency of the second ultrasonic wave differ by 0.1% to 10%.

6. The device according to claim 3, wherein the first and the second ultrasonic waves are standing waves.

7. The device according to claim 3, wherein the first and second ultrasonic waves are transient waves of similar frequency in the form of wave packets, which are shorter than the distance between the first section end and the second section end, so as to form a transient standing wave in at least part of the turbidity measurement section.

8. The device according to claim 1, wherein the first ultrasonic wave is a standing wave.

9. The device according to claim 1, wherein the control circuit is arranged to generate the signal indicative of the turbidity of the fluid in response to signals received from the receiver transducer and a flow rate of the fluid.

10. The device according to claim 1, wherein the control circuit is arranged to operate the first transducer in a first and a second operation time interval, wherein the first and second operation time intervals are not overlapping, wherein the control circuit is arranged to operate the first transducer for measuring the turbidity of the fluid flowing in the flow tube during the first operation time interval, and wherein the control circuit is arranged to operate the first transducer for measuring the flow rate of the fluid flowing in the flow tube during the second operation time interval.

11. The device according to claim 1, comprising temperature measurement means, wherein said temperature measurement means comprises the first transducer.

12. The device according to claim 1, comprising a first ultrasonic reflector arranged to guide ultrasonic signals from the first transducer in a direction of the fluid flowing in the turbidity measurement section.

13. The device according to claim 1, wherein the receiver transducer is arranged in an opening in a wall of the flow tube.

14. The device according to claim 1, comprising an acoustic lens or an aperture arranged in relation to the receiver transducer, so as to limit a volume of the turbidity measurement section from which ultrasonic signals can reach the receiver transducer.

15. An ultrasonic consumption meter comprising a device according to claim 1.

16. A system for monitoring turbidity of fluid in a utility network, the system comprising:
a plurality of devices according to claim 1, wherein each of the plurality of devices is arranged to transmit signals indicative of the turbidity of the fluid,
a communication system arranged to mediate said signals indicative of the turbidity of the fluid from the plurality of devices, and
a processor system arranged to analyze said signals indicative of the turbidity of the fluid.

17. The device according to claim 1, wherein:
the through-going opening of the flow tube defines a flow path for passage of the fluid;
the first transducer is arranged to transmit ultrasonic signals along a path through the fluid in the turbidity measurement section; and
the receiver transducer is positioned outside of the flow path of the fluid and outside of the path of the transmitted ultrasound signals.

18. A method of measuring turbidity of a fluid flowing in a turbidity measurement section of a flow tube between a first section end and a second section end of the flow tube, the method comprising:
operating a first transducer, using a control circuit, to transmit ultrasonic signals, at a first frequency for measuring the turbidity, through the fluid in the turbidity measurement section so as to provide a first ultrasonic wave between the first section end and the second section end,
operating the first transducer, using the control circuit, to transmit ultrasonic signals at a second frequency for measuring flow rate, wherein the first frequency is an odd harmonic of the second frequency,
receiving, by a receiver transducer having a receiving surface which is parallel to a propagation direction of the first ultrasonic wave, ultrasonic signals scattered on particles in the fluid flowing through the turbidity measurement section, and
generating, using a control circuit connected to the first transducer and the receiver transducer, a signal indicative of the turbidity of the fluid in response to signals received from the receiver transducer.

19. A device arranged to measure turbidity of a fluid flowing in a flow tube, the device comprising:
a flow tube having a through-going opening for passage of a fluid between an inlet and an outlet and a turbidity measurement section between a first section end and a second section end,
a first transducer arranged to transmit ultrasonic signals through the fluid in the turbidity measurement section so as to provide a first ultrasonic wave between the first and second section ends,
a receiver transducer arranged for receiving ultrasonic signals scattered on particles in the fluid flowing through the turbidity measurement section, wherein the receiver transducer has a receiving surface which is parallel to a propagation direction of the first ultrasonic wave, and a control circuit connected to the first transducer and the receiver transducer, the control circuit being arranged to operate the first transducer and to generate a signal indicative of the turbidity of the fluid in response to signals received from the receiver transducer, wherein:

the control circuit is arranged to operate the first transducer at:
    a first frequency for measuring the turbidity, and
    a second frequency for measuring flow rate;
the first frequency is higher than the second frequency; and
the first frequency is an odd harmonic of the second frequency.

* * * * *